United States Patent
Gordon

(10) Patent No.: US 6,616,677 B2
(45) Date of Patent: Sep. 9, 2003

(54) METHOD AND PROCESS FOR GENERATING A HIGH REPETITION RATE PULSED MICROJET

(75) Inventor: Eugene Gordon, Mountainside, NJ (US)

(73) Assignee: Medjet, Inc., Edison, NJ (US)

(*) Notice: Subject to any disclaimer, the term of this patent is extended or adjusted under 35 U.S.C. 154(b) by 0 days.

(21) Appl. No.: 09/886,656

(22) Filed: Jun. 21, 2001

(65) Prior Publication Data

US 2002/0007143 A1 Jan. 17, 2002

Related U.S. Application Data

(60) Provisional application No. 60/213,183, filed on Jun. 21, 2000.

(51) Int. Cl.[7] .............................................. A61B 17/32
(52) U.S. Cl. ...................................... 606/167; 604/294
(58) Field of Search ................................ 606/167, 159, 606/162, 170, 171, 185; 604/22, 19, 27, 28, 150, 151

(56) References Cited

U.S. PATENT DOCUMENTS

| | | | | |
|---|---|---|---|---|
| 3,515,130 A | * | 6/1970 | Tsujino ........................ 128/173 |
| 3,818,913 A | | 6/1974 | Wallach ....................... 128/305 |
| 4,058,123 A | | 11/1977 | May ............................ 128/278 |
| 4,660,556 A | | 4/1987 | Swinger et al. ............. 128/305 |
| 4,913,698 A | * | 4/1990 | Ito et al. ..................... 604/141 |
| 5,163,909 A | * | 11/1992 | Stewart ................ 128/DIG. 12 |
| 5,215,104 A | | 6/1993 | Steinert ....................... 128/898 |
| 5,322,504 A | | 6/1994 | Doherty et al. ............. 606/167 |
| 5,348,539 A | | 9/1994 | Herskowitz ................. 604/141 |
| 5,562,692 A | | 10/1996 | Bair ............................ 606/167 |
| 5,620,414 A | * | 4/1997 | Campbell, Jr. .............. 604/150 |
| 5,643,299 A | | 7/1997 | Bair ............................ 606/166 |
| 5,735,386 A | | 4/1998 | Epp et al. ............... 198/550.01 |
| 5,830,224 A | * | 11/1998 | Cohn et al. .................... 604/22 |
| 5,853,384 A | | 12/1998 | Bair ............................... 604/22 |
| 5,865,790 A | | 2/1999 | Bair ............................... 604/35 |
| 6,068,640 A | * | 5/2000 | Gordon et al. ............. 604/294 |
| 6,221,260 B1 | * | 4/2001 | Chahine et al. ............ 210/175 |
| 6,264,666 B1 | * | 7/2001 | Coleman et al. ............. 433/84 |

* cited by examiner

Primary Examiner—Michael J. Milano
Assistant Examiner—Victor Nguyen
(74) Attorney, Agent, or Firm—Darby & Darby

(57) ABSTRACT

A system and method for producing a high repetition pulsed microjet for use in medical applications. The device includes a stagnation chamber and a hydraulic pump for pumping a sterile fluid into the stagnation chamber. A flexible walled volume disposed in the stagnation chamber and filled with a hydraulic fluid. The hydraulic piston is cyclically displaced towards/away from the stagnation chamber thereby increasing/decreasing the pressure of the hydraulic fluid on the flexible walled volume. In turn, the flexible walled volume is compressed and the sterile fluid is expelled through an orifice in the flexible walled volume under pressure producing the pulsed microjet. This process may be repeated to produce repetitive pulsed microjets. In addition, the flow conduction of the hydraulic fluid between the hydraulic pump and stagnation chamber may be controlled by inserting a blocking device therebetween.

7 Claims, 3 Drawing Sheets

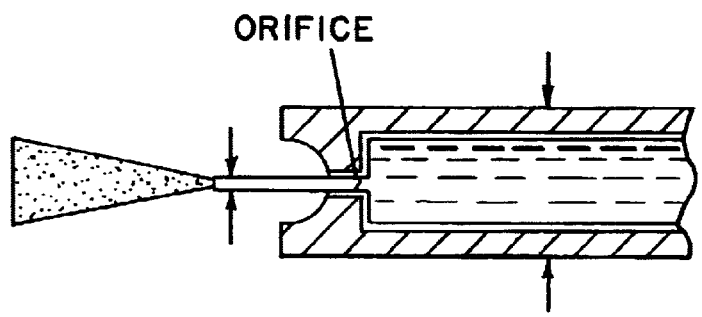
FIG. 5a
FIG. 5b
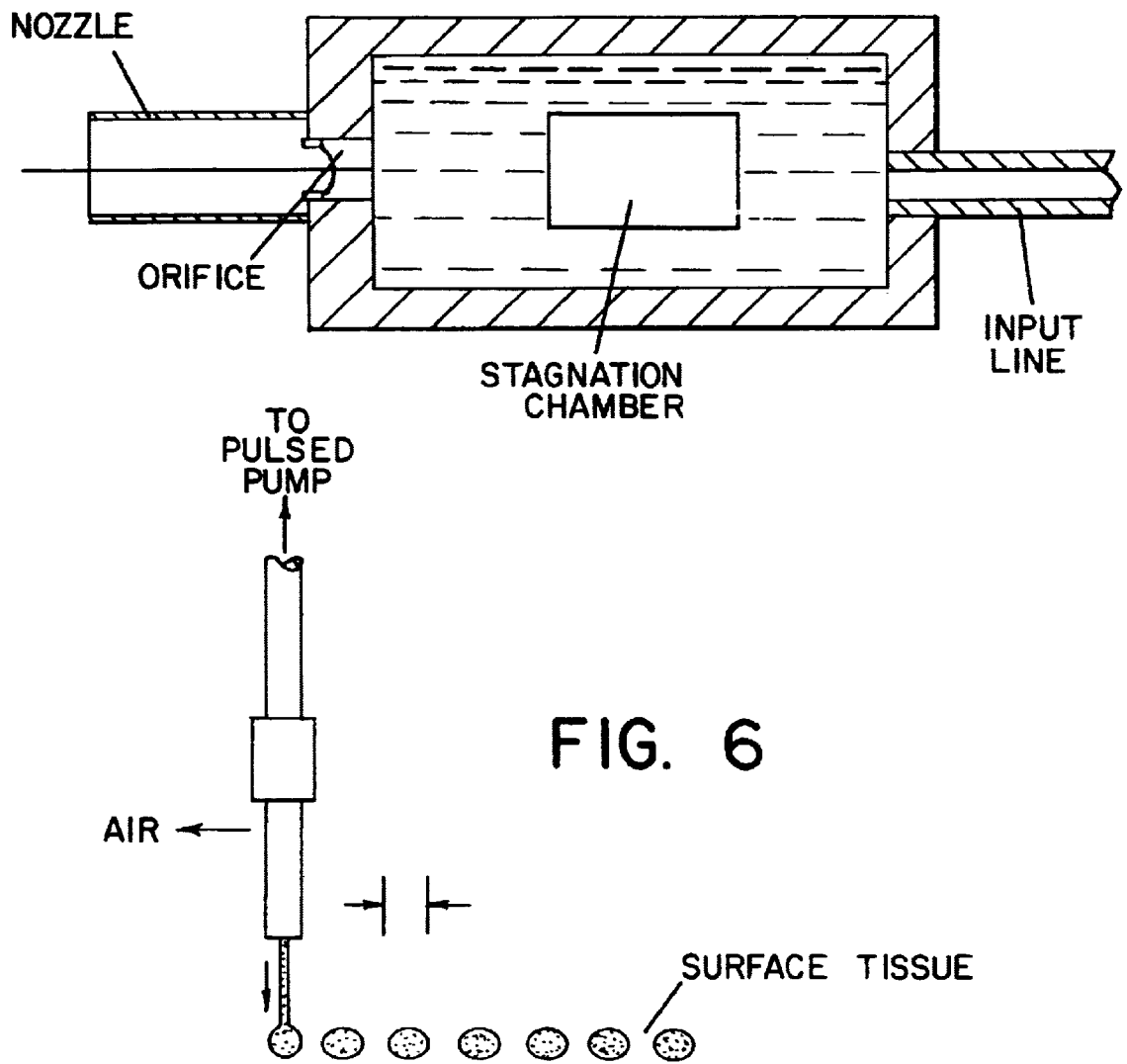
FIG. 6

METHOD AND PROCESS FOR GENERATING A HIGH REPETITION RATE PULSED MICROJET

CROSS-REFERENCE TO RELATED APPLICATIONS

This application claims the benefit of U.S. Provisional Application Serial No. 60/213,183, filed on Jun. 21, 2000, which is hereby incorporated by reference in its entirety.

FIELD OF THE INVENTION

The present invention relates to liquid jets and, in particular, to a high repetition rate pulsed microjet.

DESCRIPTION OF RELATED ART

Hypodermic needle injectors are used to introduce fluids, such as medication, anesthetic, or vaccines, subdermally. Such injectors dispense fluid into a semi-hemispherical volume of a few cubic centimeters just beneath the skin. Accordingly, 1 cc, which is equivalent to 1 ml=$10^3$ $\mu$L=$10^3$ mmd$^3$, of injected fluid occupies an approximately hemispherical volume of $(2\Pi/3)R^3$, where the radius R is approximately 0.8 cm.

Liquid jet injectors have been used as an alternative to a hypodermic needle injectors. The liquid jet injectors ("microjets") inject a small, coherent, circular diameter of a predetermined amount of fluid subdermally or a predetermined depth into the tissue. Any type of fluid may be used such as drugs or vitamins. The injected fluid is pulsed for a predetermined period of time. Pulses may be repeated at a predetermined repetition rate to cover an area, to accurately administer a larger dose, or to aid in breaking up of the tissue. Typically, the repetition rate is between several pulses to several thousand pulses per second.

Liquid jet injectors typically pressurize the fluid using $CO_2$ liquid that is vaporized. Conventional liquid jet injectors operate at relatively low pressure at approximately 850 psi and produce a few milliliters of fluid volume with every pulse.

It is therefore desirable to develop a device for producing a high repetition pulsed microjet of reduced spherical volume and higher pressure than conventional liquid jet injectors.

SUMMARY OF THE INVENTION

An object of the present invention is to develop a system for producing a repetitive pulsed microjet able to precisely measure doses of relative small spherical volume, for example, preferably between approximately 1 $\mu$L and approximately 10 $\mu$L (which is equivalent to approximately 1 mm$^3$ to approximately 10 mm$^3$), with each pulse to a predetermined depth into the tissue or beneath the skin.

Another object of the present invention is to develop a device for producing a repetitive pulsed microjet to inject pulses of energy into tissue instead of conventional pulsed lasers.

The present invention is also directed to developing a method for using a device to produce repetitive pulsed microjets to be used as an alternative to ultrasonic transducers in cataract removal surgery.

Another object of the invention is to use the device to administer heated fluids beneath the surface of the skin.

The present invention relates to a system and method for producing a high repetition pulsed microjet for use in medical applications. The device includes a stagnation chamber and a hydraulic pump for pumping a sterile fluid into the stagnation chamber. A flexible walled volume disposed in the stagnation chamber is filled with a hydraulic fluid. The hydraulic piston is cyclically displaced towards/away from the stagnation chamber thereby increasing/decreasing the pressure of the hydraulic fluid on the flexible walled volume. In turn, the flexible walled volume is compressed and the sterile fluid is expelled through an orifice in the flexible walled volume under pressure producing the pulsed microjet. This process may be repeated to produce repetitive pulsed microjets. In addition, the flow conduction of the hydraulic fluid between the hydraulic pump and stagnation chamber may be controlled by inserting a blocking device therebetween.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIGS. 5a and 5b are exemplary nozzle configurations; and

FIG. 6 is a diagram depicting the use of the pulse microjet for use in the treatment of collagen shrinkage.

DETAILED DESCRIPTION OF THE INVENTION

Figure 1:
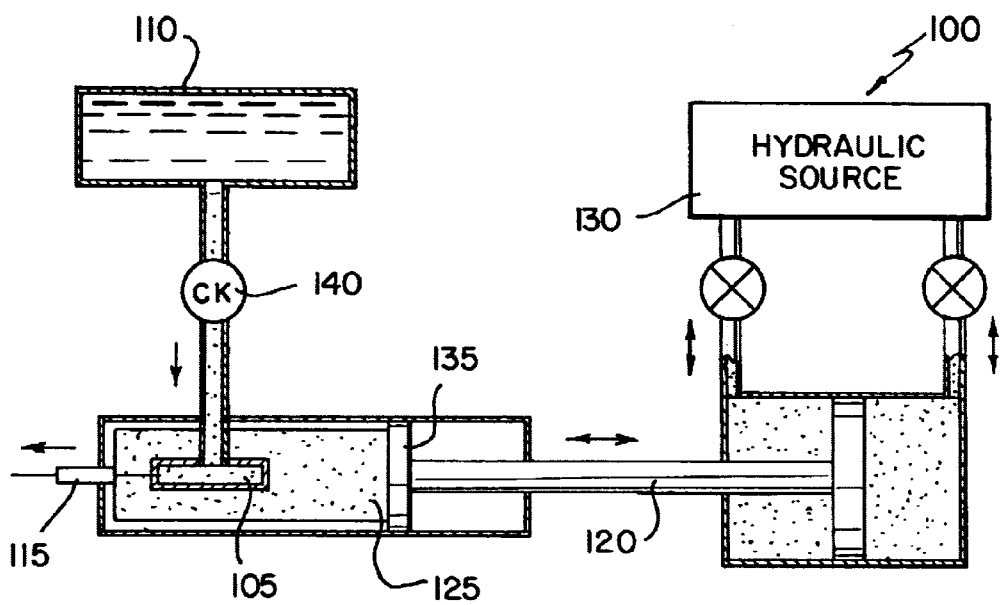
FIG. 1 is a device for producing a repetitive pulsed microjet in accordance with the present invention.

An exemplary system for producing a short pulsed microjet in accordance with the present invention is shown in FIG. 1. A flexible walled volume (FWV) or flexible bladder 105 contains a fluid, preferably a sterile fluid, under pressure and an orifice 115. FWV 105 is immersed in a hydraulic fluid. The FWV is manufactured from a material that is compatible with the hydraulic and sterile fluids, and is flexible enough to sustain repetitive squeezing and cycling, such as stainless steel or plastic. The surgical fluid in the FWV 105 is received from a reservoir 110. A check valve 140 or similar device is preferably disposed between the reservoir 110 and FWV 105 to ensure flow in a single direction. A piston-driven hydraulic pump 120 is connected to a hydraulic source 130. As the piston 135 is displaced towards the FWV, the hydraulic fluid is compressed exerting pressure on the outer surface of the FWV that produces a continuous microjet through orifice 115. Electrical and/or mechanical valves control the motion of the piston. The volume in bladder 105 is prefixed so regardless of how much the pump 120 compresses the hydraulic fluid surrounding the FWV 105 at most the prefixed volume of fluid in the FWV is expelled. Hence the liquid dispensed with each pulsed microjet is precisely determined.

To produce a pulsed microjet, the piston 135 is moved away from the FWV 105 thereby reducing the pressure of the hydraulic fluid within the hydraulic pump 120 below atmospheric pressure and drawing the surgical fluid into the FWV 105 from the reservoir 110 through the check valve 140. Atmospheric air pressure above the sterile fluid in the reservoir 110 forces the sterile fluid into the FWV 105. If necessary, the pressure above the sterile fluid in the reservoir may be increased above atmospheric pressure to improve the filling rate. When the direction of movement of piston 135 is reversed by moving toward the FWV 105, the hydraulic fluid and sterile fluid are compressed to approximately the same stagnation pressure. The stagnation pressure is determined by the pressure of the hydraulic fluid driving the piston forward and the intensifier ratio. Despite the stagnation pressure, flow of the sterile fluid back to the reservoir 110 is prevented by the check valve 140. The pressurized sterile fluid in the FWV 105 is ejected through the orifice 115 as a result of the stagnation pressure producing a transient microjet beam. Preferably, the hydraulic and sterile fluids are substantially incompressible, otherwise the rise and fall times of the microjet pulse will be drawn out. Displacement of the piston 135 is a similar manner to that described above is repeated for each microjet pulse. The volume of fluid with each pulse is based on the volume of the FWV 105 and/or the stop positions of the piston 135.

Microjets are advantageous over pulsed subdermal lasers in the duration of the pulse, volume of fluid, the area of dispersion of the fluid, and the depth to which the fluid is injected below the skin or tissue surface. By way of example, each microjet pulse can produce a pulse approximately 10 millisecond in duration of approximately 10 microliters of fluid producing an approximately 50 micron to approximately 100 micron diameter spot into the tissue. Larger volumes or longer pulses may be generated, as desired. Parameters may be varied for each particular application. The microjet pulse produces up to approximately 1 joule of energy and can readily produce a peak local temperature rise between approximately 80degrees Celsius to approximately 100 degrees Celsius, or more depending on the requirement. The volume, diameter, pulse length, and thermal conductivity of the tissue determine the actual peak temperature rise for a given input energy and the transient temperature behavior. The energy input includes the beam kinetic energy and thermal energy of the sterile fluid. Depending on the stagnation pressure, the kinetic energy component can be significant. The temperature of the sterile fluid is readily controlled. The pulse repetition rate can be several pulses per second. The stagnation pressure controls the subdermal depth of the fluid being injected. Although local cooling is also possible, the kinetic energy of the sterile fluid is significant. Accordingly, the sterile fluid is preferably cooled, as least somewhat, as it is expelled from the orifice 115.

Microjets are also advantageous in that they can be repetitively pulsed at a natural frequency of up to approximately 1000 Hz, limited by the natural fluid flow instabilities in the formation of the microjet that prevent higher frequencies from being achieved. Beyond the natural frequency, pulsing occurs without external control and the microjet does not have a consistent modulation depth and controlled repetition rate. These natural instabilities can be avoided by lowering the repetition rate, however, controlling the repetition rate impacts how effectively the targeted object, e.g., cataract nucleus, is broken up. Ultrasonic systems are typically pulsed at a rate of 25 KHz. Microjets are generally pulsed at a much lower rate. However, because the microjet is able to deliver much greater impact energy per pulse, for example, in the order of between approximately 10 and approximately 100 times greater than an ultrasonic system, the greater impact energy more than compensates for the reduced impact rate. In addition, the microjet delivers thermal energy directly to the targeted object with little, if any, spatial dispersion.

Yet another advantage associated with the microjet needle injector is the ability to control flow conduction. Control of the microjet pulse profile and repetition rate is achieved by controlling flow conduction. Orifice 115 has a predetermined flow rate. When the flow conductivity at the hydraulic pump 120 relative to the orifice 115 is large, then the flow rate through the orifice is substantially controlled only by the orifice conductivity and the stagnation pressure. In this case the stagnation pressure at the orifice is substantially equal to the pump pressure, less a small pressure drop due to resistance in the conductivity path. On the other hand, when the flow conductivity at the hydraulic pump 120 relative to the orifice 115 is small, then the flow rate through the orifice is controlled by the flow path resistance. In this scenario, the stagnation pressure is significantly less than the pump pressure and the microjet is effectively turned off.

Figure 2:
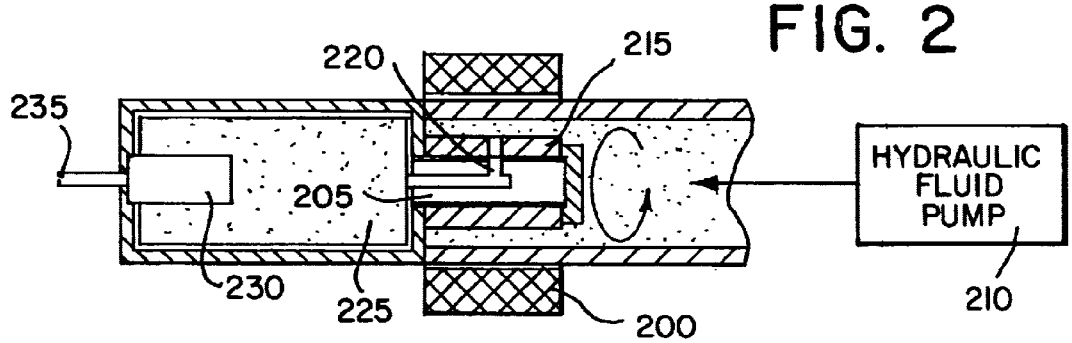
FIG. 2 is a ball valve used to control flow conduction.

Many different techniques can be used to modulate the microjet output from the orifice to achieve the repetitive pulsing advantages of the microjet. A variety of different types of mechanical and/or electrical blocking devices may be used to control flow conduction between the hydraulic fluid pump and the compression or stagnation chamber. One technique for controlling the flow conductivity is to use an electronically controlled ball valve, such as that shown in FIG. 2. A stationary center tube 205 connects the hydraulic fluid pump 210 with the stagnation chamber 225. A stator 200 generates magnetic impulses to rotate a magnetic armature/ball 215 valve at a desired rate, consistent with the desired pulse repetition rate of the microjet from the orifice 235.

If one opening is defined in the armature 215, then the pulse repetition rate and rotation rate are equal. Depending on the number of openings in the stationary center tube and the rotation rate, the flow conductivity from the hydraulic fluid pump 210 to the compression chamber 225 is a predetermined number of times per second. Each time a pair of openings is aligned, the stagnation pressure in the compression chamber 225 rises to a value approximately equal to the pump pressure. The hydrostatic pressure within the FWV 230 rises to substantially equivalent to the pressure of the hydraulic fluid in the stagnation chamber 225 and a high-speed microjet originates from the orifice 235. The pulse repetition rate is calculated as the rotation rate times the number of openings in the stationary center tube. By way of example, if the rotation rate of the armature 215 is 60 rps and the stationary center tube has 16 openings defined therein, the pulse repetition rate would be 960 pps.

Figure 3A:
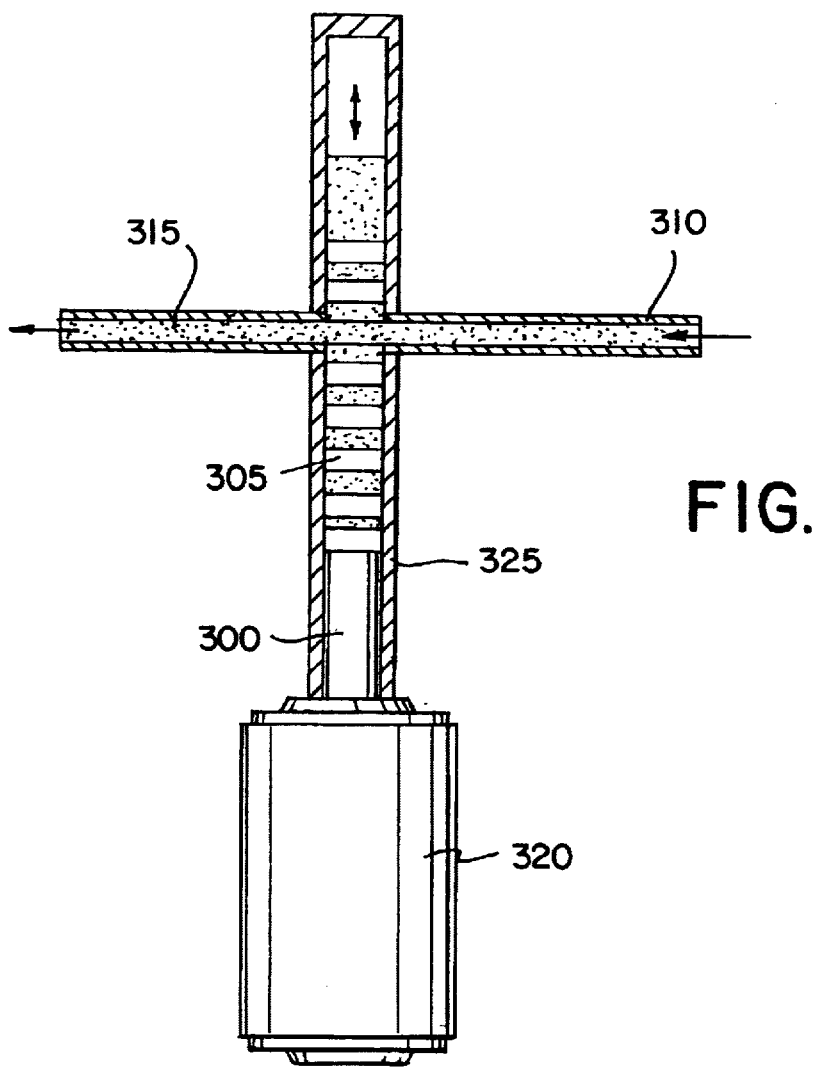
FIG. 3a is a circular cylindrical armature shaft to control flow conduction.
Figure 3B:
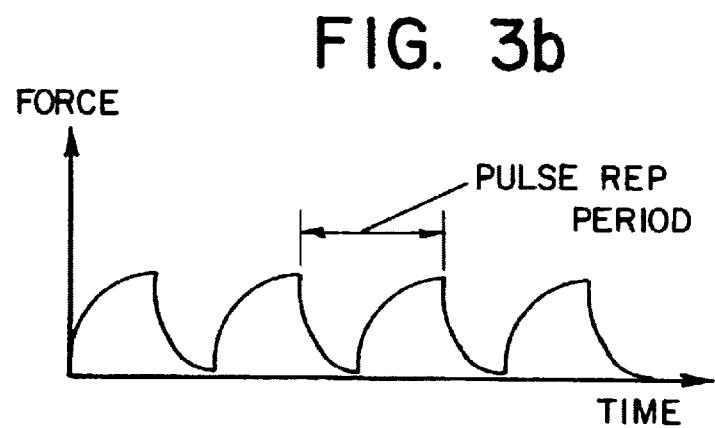
FIG. 3b is a timing diagram showing a time constant for build up and decay of the stagnation pressure in the compression chamber.

Alternatively, a circular cylindrical armature shaft can be used to control flow conduction, as shown in FIG. 3. A non-rotating armature shaft 300 is displaced linearly, as depicted by the arrows, within a tight-fitting cylindrical housing 325 by linear motor 320. As the armature shaft 300 is repetitively displaced back and forth in a linear movement at a substantially constant speed, openings 305 defined in armature shaft 300 are aligned juxtaposition with the conduction path and allow the flow conduction from the hydraulic pump 310 to the stagnation chamber 315. As a result the stagnation pressure in the stagnation chamber 315 increases and exerts pressure on the FWV that causes the fluid to be ejected from the orifice as a pulsed microjet. On the other hand, when an opening is not aligned with the conduction path the flow conduction is blocked. Residual flow conductivity is present around the armature path, which preferably fits tightly within housing 325. The tighter the fit of the armature shaft 300 within the housing 325, the lower the residual conductivity at the armature path. When the flow conductivity is low, the stagnation pressure decays and the microjet loses force and flow rate. Control of alternating flow conductivity, for example, low to high and back to low, allows periodic increases in fluid pressure in the stagnation chamber 315. The increased stagnation chamber pressure is relieved when the conduction path is blocked again. In addition, the reduction in volume of the FWV as the sterile fluid is expelled through the orifice decreases the pressure in the stagnation chamber 315. In an alternative embodiment, the armature shaft 300 may be driven by a lead screw which, in turn, is driven by a rotating motor, instead of a linear motor 320.

If the hydraulic fluid and surgical fluid are completely incompressible, and the surrounding conduction paths are rigid, the stagnation pressure will rise instantly as a conduction path defined through the armature comes into juxtaposition with the fixed opening in the housing 324 and a constant flow of fluid is expelled from the orifice. Once the opening is displaced and no longer aligned, the stagnation pressure in the stagnation chamber drops as quickly as it rose. Accordingly, the fluid microjet pressure pulses would be represented by a square waveform. In actuality, the fluids are slightly compressible and the walls are not entirely rigid. Hence a time constant exists for build up and decay of the stagnation pressure in the compression chamber, for example, as represented by the timing diagram in FIG. 3*b*. The flow through the orifice in combination with the energy storage is the defining factor for the decay time. Preferably, the system is designed so that the time constant for the pulse is small, for example, 1/10th of the pulse repetition period. Such a system provides virtually 100% pressure modulation and maximum hammering force. However, the system may be designed having a different time constant with the upper limit being approximately 10,000 pps.

Figure 4:
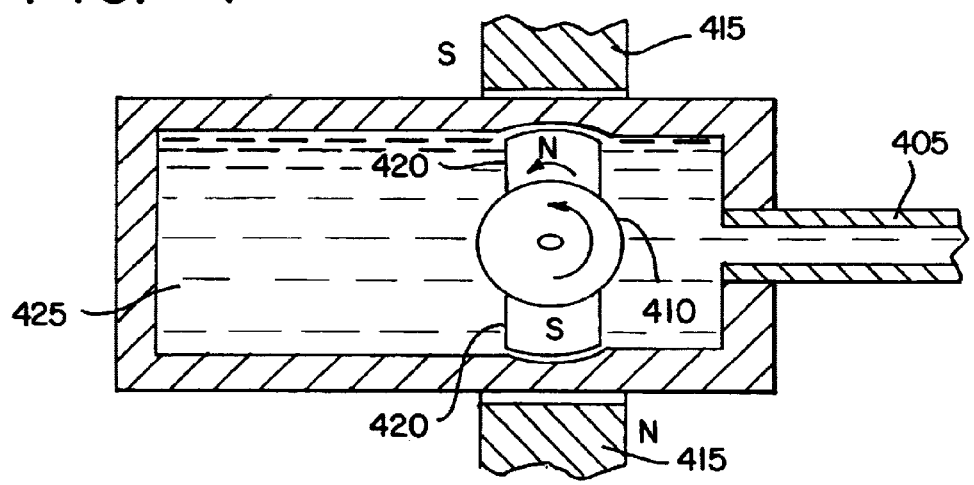
FIG. 4 is an internal rotor made of magnets to control flow conduction.

FIG. 4 is an alternative configuration of a blocking mechanism to control flow conduction. An internal rotor 410 made of magnets is disposed in a circular housing and driven externally by rotating or alternating magnetic fields 415. The rotation of the rotor periodically brings two vanes 420 close to the internal walls of the stagnation chamber 425. The stagnation chamber 425 is made of a non-magnetic material such as stainless steel. Preferably, the gap between the vanes 420 and the inner walls of the stagnation chamber 425 is just wide enough to permit free rotation of the rotor 410. Rotation of the rotor periodically modifies flow conductance. Since the orifice can continue to produce a microjet flow, the stagnation pressure on the orifice side of the chamber drops precipitously whenever the flow conductance is decreased. The decrease occurs whenever the vanes are close to the internal walls of the stagnation chamber 425. This gives rise to a pulsating microjet being expelled through the orifice.

The device for producing a microjet in accordance with the present application has varied applications in the medical field. One such application is to be used for accurate subdermal or endoscopic injection of fluid, such as drugs, antibiotics, chemotherapy, or vitamins. Subdermal injections may dispense heated fluids that have such useful applications as to shrink collagen or increase the efficiency of chemotherapy drugs. Collagen shrinks when heated to approximately 70 degrees Celsius. As a result, the heated collagen tensions the skin and reduces wrinkles. FIG. 6 is a diagram depicting the use of the pulsed microjet during collagen shrinkage treatment. It has also been recognized that injection of chemotherapy drugs at an increased temperature is beneficial in that it enhances the delivery of the drug to the specific site and efficacy of the chemotherapy with a reduced dosage thereby lessening the toxic side effects.

Another useful medical application of the device for producing a pulsed microjet in accordance with the present application is in the removal of cataracts. A cataract is a serious eye disease leading to eventual blindness. The eye consists of a capsule. The capsule is a circular, flat, thin-walled bag with membrane-like walls. Within the capsule is a complex structure known as the nucleus. The nucleus fills the capsule and is attached to its inner surfaces. Attached to the external, perimetric boundary of the capsule are zonules (string-like tissue) that couple the capsule perimeter to ciliary muscles. Depending on the state of tension in the ciliary muscles, the capsule may be almost flat or highly convex in shape. The nucleus is springy and tends to provide an outward convex shaping force. The shape of the capsule determines its refractive power. Hence the ciliary muscles control the adjustment of the total refractive power of the lens system of the eye. This adjustable feature is referred to as accommodation.

The nucleus grows throughout a persons life and eventually the ability of the ciliary muscles to adjust focusing diminishes. This effect is call presbyopia. Ultimately, the nucleus may become hard and opaque causing cataracts. Cataract surgery removes most of the anterior (front) membrane of the capsule, breaking up the inner nucleus into small fragments which are aspirated along with the tissue associated with attachment of the nucleus to the inner posterior wall of the capsule. A plastic convex lens of an appropriate refractive power is then inserted into the remaining capsule to provide a refractive power sufficient to sharply focus objects at a distance on to the retina. Thereafter, there is no residual accommodation.

There is great interest in reducing the cost of the procedure. In the U.S., the cost has dropped from about $3,000 to about $800 per eye. Hence, there is a great demand for cost-effective, cataract surgery equipment that requires less skill and surgical time.

A short pulse high repetition rate fluid jet having a precise stagnation pressure is an effective new technique for removing cataracts quickly and harmlessly with minimal injection fluid and requiring a relatively small diameter nozzle. Preferably the short pulse is one millisecond and having a repetition rate of hundreds or thousands of pulses per second. The staccato nature of the intense impulsive force effectively breaks up the nucleus into small pieces more effectively than ultrasonic energy. In addition, the thermal input may be low so as not to produce significant heating of the tissue, a common problem with the conventional ultrasonic approach.

With a liquid jet, a jewel, such as a ruby or sapphire, having a circular orifice may be used to produce high pressure pulses by providing a collimated beam of fluid that maintains coherence over a significant distance. FIG. 5*a* depicts such a nozzle. However, since the microjet in accordance with the present invention may be designed so that the nozzle is virtually in contact with the nucleus an inexpensive material, such as quartz or stainless steel, may be adequate to break up the nucleus because coherence of the collimated beam does not have to be maintained over a significant distance. Such tubes may be tapered and have diameters of preferably approximately 500 microns at its wider end and approximately 50 microns at the smaller end, and preferably has a length of several millimeters. FIG. 5*b* is an exemplary embodiment of this alternative nozzle configuration in accordance with the present invention. In the stagnation volume, the flow density is low and the flow lines must set up precisely to allow a coherent, continuous, microjet stream.

The other medical applications in which the pulsed microjet may find suitable application are limitless. Some additional applications include localized freezing and hydrocoagulation of blood. Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily to scale, but that they are merely conceptual in nature. It is the intention, therefore, to be limited only as indicated by the scope of the claims appended hereto.

What is claimed is:

1. A method for producing a repetitively pulsed microjet using a device including a flexible walled volume containing a first fluid, said flexible walled volume being disposed within a stagnation chamber and a hydraulic pump for pumping a second fluid into said stagnation chamber, comprising the steps of:

(a) filling the flexible walled volume with the first fluid;

(b) increasing the pressure of the second fluid in the stagnation chamber and around the flexible walled volume;

(c) dispensing the first fluid from an orifice defined in the flexible walled volume as a pulsed microjet; and (d) repeating steps (a) to (c) whereby a pulsed output is produced.

2. The method in accordance with claim 1, further comprising the step of:

(d) decreasing the pressure of the second fluid in the stagnation chamber around the flexible walled volume;

(e) refilling the flexible walled volume with the first fluid;

(f) increasing the pressure of the second fluid in the stagnation chamber around the flexible walled volume;

(g) dispensing the first fluid from an orifice defined in the flexible walled volume as a pulsed microjet; and (h) repeating steps (d) through (g) a plurality of times to generate a repetitive pulse microjet.

3. The method in accordance with claim 1, wherein said first fluid is heated to a predetermined temperature above room temperature.

4. The method in accordance with claim 1, further comprising the step of cooling the dispensed first fluid.

5. The method in accordance with claim 1, wherein in step (b) the first and second fluids are at substantially the same pressure.

6. The method in accordance with claim 1, wherein the first and second fluids are substantially incompressible.

7. The method in accordance with claim 1, wherein step (b) comprises displacing a piston associated with the hydraulic pump towards the flexible walled volume.

* * * * *